*(12)* United States Patent
Misevic

(10) Patent No.: US 7,501,402 B2
(45) Date of Patent: Mar. 10, 2009

(54) FUCOSE CONTAINING PROTEOGLYCAN OR ACIDIC GLYCAN AND THEIR PHARMACEUTICAL USE

(76) Inventor: Gradimir Misevic, Hermann Albrecht Strasse 15, 4058 Basel (CH)

( * ) Notice: Subject to any disclaimer, the term of this patent is extended or adjusted under 35 U.S.C. 154(b) by 448 days.

(21) Appl. No.: 10/423,855

(22) Filed: Apr. 25, 2003

(65) Prior Publication Data

US 2005/0197318 A1 Sep. 8, 2005

Related U.S. Application Data

(63) Continuation-in-part of application No. 09/731,092, filed on Dec. 6, 2000, now Pat. No. 6,596,689, which is a continuation-in-part of application No. 08/704,777, filed as application No. PCT/IB95/00208 on Mar. 24, 1995, now abandoned.

(30) Foreign Application Priority Data

Mar. 24, 1994 (GB) .............................. 94-05 846.8

(51) Int. Cl.
*A61K 31/737* (2006.01)
*C12P 19/04* (2006.01)
*C07H 3/06* (2006.01)
(52) U.S. Cl. ........................................ 514/54; 536/123
(58) Field of Classification Search .................. 514/54; 536/55.1
See application file for complete search history.

(56) References Cited

OTHER PUBLICATIONS

Papakonstantinou et al., "Isolation and Characterization of a New Class of Acidic Glycans Implicated in Sea Urchin Embryonal Cell Adhesion" Journal of Cellular Biochemistry (1993) vol. 53, pp. 98-113.*

Misevic et al., "The Species-specific Cell-binding Site of the Aggregation Factor from the Sponge *Microciona prolifera* Is a Highly Repetitive Novel Glycan Contaning Glucuronic Acid, Fucose, and Mannose." The Journal of Biological Chemistry (1990) vol. 265, No. 33, pp. 20577-20584.*

Henkart et al., "Characterization of Sponge Aggregation Factor. A Unique Proteoglycan Complex" Biochemistry (1973) vol. 12, No. 16, pp. 3045-3050.*

Haseley et al., "Carbohydrate self-recognition mediates marine sponge cellular adhesion" Proc. Natl. Acad. Sci. (2001) vol. 98, No. 16, pp. 9419-9424.*

Oxford Textbook of Oncology, published 1995 by Oxford University Press, pp. 447-453.*

* cited by examiner

*Primary Examiner*—Shaojia Anna Jiang
*Assistant Examiner*—Eric S Olson

(57) ABSTRACT

A class of proteoglycans containing fucosylated acidic glycans, e.g., as produced by marine sponges and sea urchin embryos, have been found to stimulate selective proliferation of mammalian natural killer (NK) cells and γδT cells. These compounds are useful as pharmaceuticals, particularly as immunostimulants, e.g., in the treatment of cancer and viral infections.

10 Claims, No Drawings

FUCOSE CONTAINING PROTEOGLYCAN OR ACIDIC GLYCAN AND THEIR PHARMACEUTICAL USE

CROSS-REFERENCE TO RELATED APPLICATIONS

This application is a Continuation-In-Part Application of U.S. patent application Ser. No. 09/731,092, now U.S. Pat. No. 6,596,689, Filed: Dec. 6, 2000. entitled "Fucose Containing Proteoglycan or Acid Glycan and Their Pharmaceutical Use" which was a Continuation-In-Part Application of U.S. patent application Ser. No. 08/704,777, now abandoned, filed Dec. 13, 1996, entitled "Fucose Containing Proteoglycan or Acid Glycan and Their Pharmaceutical Use" which is a national phase application under U.S.C. § 371 of PCT/IB95/00208 filed Mar. 24, 1995 which claims priority of United Kingdom Application No. GB 94-05 846.8 filed Mar. 24, 1994, the disclosures of which is hereby incorporated by reference in its entirety.

STATEMENT REGARDING FEDERALLY SPONSORED RESEARCH OR DEVELOPMENT

Not Applicable

BACKGROUND OF THE INVENTION

1. Field of the Invention

This invention relates to a class of proteoglycans having fucosylated acidic glycan side chains bound to a protein backbone which have been found to stimulate selectively proliferation of natural killer (NK) cells and/or γδT cells. They are useful as immunostimulants, e.g., in the treatment of cancer and viral infections.

2. Description of the Related Art

The proteoglycans of the invention are produced by proliferating cells, for example by sponge cells, sea urchin cells, and, in the case of higher animals (including humans), by embryonic cells and tumor cells. In the natural proteoglycan form, the compounds are large (ca. 5000 to 30,000 kD) extracellular or membrane-bound molecules having a protein backbone which is glycosylated with acidic glycan chains having an unusual polysaccharide sequence containing internal fucose. The structure of the acidic glycan side chains of the proteoglycan isolated from the marine sponge *Microciona prolifera* has been partially characterized (Spillmann, et al., J. Biol. Chem. (1993) 268: 13378-13387, contents incorporated herein by reference), and we have previously shown that this proteoglycan is involved in cellular aggregation (Misevic, et al., J. Biol. Chem. (1987) 262: 5870-5877; Misevic, et al., J. Biol. Chem. (1990) 265: 20577-20584; Misevic, et al., J. Biol. Chem. (1993) 268: 4922-4929, contents of all of these articles incorporated herein by reference). The previously undescribed protein backbone of the *Microciona prolifera* proteoglycan has now been isolated and characterized, and novel proteoglycans derived from sponges of other genera have also been characterized, as described below.

Those concerned with these and other problems recognize the need for an improved fucose containing proteoglycan or acidic glycan and their pharmaceutical use.

BRIEF SUMMARY OF THE INVENTION

It has now surprisingly been discovered that these compounds are potent stimulators of NK cells and γδT cells. In particular, compounds of the invention isolated from an organism of all the phyla and preferably:

from organisms of the Phylum Porifera e.g., of the class Demospongiae, especially of the order Poecilosclerida, family Microcionidae (e.g., of the genus *Microciona*), or family Mycalidae (e.g., of the genus *Mycale*), or the order Halichondrida, family Halichondridae (e.g., of the genus *Halichondria*), or the order Hadromerida, family Clionidae (e.g., of the genus *Cliona*), or the order Haplosclerida, family Haliclonidae (e.g., of the genus *Haliclona*), and/or from organisms of the phylum Echinodermata.

These compounds have been shown to stimulate selectively different clones of NK cells and T cells. Moreover, it has been found that compounds of the invention have significant anticancer, especially antimetastatic, effects in vivo. It is believed that these anticancer effects are due to stimulation in vivo of NK cells and/or γδT cells. The precise mechanism of this stimulation is unclear, but without intending to be bound by a particular theory, we suggest that these cells may be stimulated by polyvalent interactions with fucosylated acidic glycans of the class described herein and in this way can identify and destroy hyperproliferating cells expressing similar glycan structures. In a pathogenic case, where the hyperproliferating cells are not destroyed in this manner, it is believed that although the hyperproliferating cells produce these acidic glycans, they shed them or present them in monovalent form or other nonstimulatory or inhibitory form, thereby evading detection and destruction by NK cells and/or γδT cells specific for such acidic glycans. Application of the compounds of the invention stimulates NK cells and/or γδT cells specific for such cancer cells, thereby leading to their destruction. Additionally, the compounds of the invention are useful for stimulating NK cells and/or γδT cells against viral or retroviral infections. Finally, in monovalent form, the compounds of the invention are useful for inhibiting the activation of NK cells and/or γδT cells, thereby finding utility as immunosuppressants.

The compounds of the invention are selective in their action, in that particular compounds of the invention stimulate only particular clones or subpopulations of NK cells or γδT cells. No significant stimulation of B cells or γδT cells is observed, so undesirable immunostimulation, e.g., an allergenic or autoimmune response, is avoided. Despite this selectivity, all humans tested, from a variety of ethnic and racial groups, have cell populations capable of being significantly stimulated by the compounds of the invention. Compounds having the glycan structures of the class described herein are found in a wide variety of hyperproliferating cells from sponges to human tumors, thus the basic structure of the compounds is highly conserved. It is hypothesized that compounds of the class described herein act as signals for stimulating the body's defenses against unwanted proliferation of cancerous or infected cells, and that cancers or resistant viral infections may arise when, as described above, these compounds are secreted in nonstimulatory form. Among the examples described herein, it is noted that compounds of the invention isolated from those of the genus *Microciona* are more effective in stimulating NK cells, as described in example 1 below, whereas compounds isolated from the genus *Halichondria* are more effective in stimulating γδT cells, as described in example 9, thus selectivity among cell types receptive to this stimulation is also possible.

Other objects, advantages, and novel features of the present invention will become apparent from the following detailed description of the invention when considered in conjunction with the accompanying drawings.

DETAILED DESCRIPTION OF THE INVENTION

The invention thus provides

1. Fucose-containing proteoglycans and acidic glycans, and/or fragment(s) thereof, preferably proteoglycans, e.g., isolated or capable of being isolated from embryonic or neoplastic tissue or from an organism of all the phyla and preferably from an organism of the phylum Porifera, e.g., as described above, especially of the genera *Microciona* and/or *Halichondria* and/or *Mycale* and/or *Cliona* and/or from an organism of the phylum Echinodermata especially of the genus *Lytechinus* for use as a pharmaceutical or therapeutic agent in vivo or for ex vivo therapy; and pharmaceutical compositions comprising such compounds in combination with a pharmaceutically acceptable carrier or diluent.

2. Novel fucose-containing proteoglycans and acidic glycans, and or fragments thereof, preferably proteoglycans, isolated or capable of being isolated from organisms of the genus *Halichondria* and/or *Mycale* and/or *Cliona*.

3. Novel fucose-containing acidic glycans capable of being isolated from a sea urchin of the genus *Lytechinus*, 4. A Fucose-containing acidic glycan for use as a pharmaceutical or therapeutic agent in vivo or for ex vivo therapy; and pharmaceutical compositions comprising such compounds in combination with a pharmaceutically acceptable carrier or diluent; and capable of binding to monoclonal antibodies of the type of these named "Block 2" and described in the reference "Misevic; et al., J. Biol. Chem.(1993). 268: 4922-4929, 5. A method of stimulating the proliferation of mammalian, e.g., human, NK cells and/or γδT cells comprising contacting said cells with a compound of the invention (a fucose-containing proteoglycan and acidic glycan, and/or fragment thereof, preferably a proteoglycan and/or fragment(s) thereof, e.g., isolated or capable of being isolated from embryonic or neoplastic tissue or from an organism of the phylum Porifera, or Echinodermata e.g., as described above, especially of the genera *Microciona* and/or *Halichondria* and/or *Mycale* and/or *Cliona*, and/or of the phylum Echinodermata especially of the genus *Lytechinus*, in an ex vivo setting or in vivo, e.g., as a vaccine; or a method of treating cancer (e.g., preventing or inhibiting onset, growth, or metastasis of a tumor); or treating or preventing a viral or retroviral infection, in a mammal, e.g., man; comprising administering a pharmaceutically effective amount of a compound of the invention to a patient in need of such treatment; or the use of a compound of the invention in the manufacture of a medicament for treatment or prevention of cancer or viral or retroviral infections.

6. The use of a fucose-containing proteoglycan or acidic glycan, or fragment thereof, preferably a proteoglycan and/or fragment(s) thereof, e.g., isolated or capable of being isolated from embryonic or neoplastic tissue or from an organism of the phylum Porifera and/or Echinodermata, e.g., as described above, especially of the genera *Microciona* and/or *Halichondria*, and/or *Mycale* and/or *Cliona* for the phylum Porifera, especially of the genus *Lyiechinus* for the phylum Echinodermata for ex vivo stimulation of proliferation of NK cells and/or γδT cells.

7. A method for screening for or detecting an immunosuppressive (e.g., NK cell and/or γδT cell) inhibitory compound comprising measuring proliferation of NK cells and/or γδT cells in a system containing an NK cell or γδT cell stimulatory concentration of a compound of the invention in the presence and absence of a test compound; and compounds identified using such a method.

8. A gene coding for a protein capable of post-translational glycosylation to form the proteoglycan of the invention, vectors containing such a gene, and transformed cells, especially (i) production cells, e.g., sponge cells, incorporating such a gene for use in producing the desired proteoglycan at enhanced levels or (ii) cancer cells removed from a patient, transformed with the gene so as to express the proteoglycan in stimulatory form, irradiated, and reintroduced into the patient. The gene for *Microciona* proteoglycan can be isolated, for example, using oligonucleotide probes of a cDNA library based on the disclosed amino acid sequences.

Appropriate dosages of the compounds of the invention will of course vary, e.g. depending on the condition to be treated (for example the disease type or the nature of resistance), the effect desired, and the mode of administration. In general however satisfactory results are obtained on administration orally, rectally, nasally, topically, or parenterally, e.g. intravenously, for example by i.v. drip or infusion, at dosages on the order of from 0.01 to 2.5 up to 5 mg/kg, e.g. on the order of from 0.05 or 0.1 up to 1.0 mg/kg. Suitable dosages for patients are thus on the order of from 0.5 to 125 up to 250 mg i.v., e.g. on the order of from 2.5 to 50 mg i.v. Pharmaceutical compositions of the invention may be manufactured in conventional manner, in a suitable aqueous carrier, for example sterile buffered physiological saline.

For ex vivo stimulation of cells, as described more fully in the example below, a suitable amount, e.g., at least 10 ml, of the patient's blood is removed, peripheral blood mononuclear cells are isolated from the blood, placed in a complete medium in the presence of a stimulatory concentration of a compound of the invention, e.g., 10-500 μg/ml, ca. 100 μg/ml, optionally in the presence of IL-2, and the culture is maintained until a significant increase in the population of the desired cell type is observed, e.g., ca. 2-4 weeks. Following stimulation of the cells, the cells are isolated from the medium, placed in an injection solution, e.g., sterile buffered physiological saline or plasma, and injected back into the patient. The compound of the invention for this use can, for example, be a proteoglycan or acidic glycan derived from a marine sponge as described in the examples, but may also be a proteoglycan, acidic glycan or fragment thereof isolated from a culture of the cancerous cells to be treated.

INDUSTRIAL APPLICATION

The compounds can be useful notably as pharmaceuticals, particularly as immunostimulants, e.g. in the treatment of cancer and viral infections.

EXAMPLE 1

Preparation of Proteoglycan and Acidic Glycans from *Microciona prolifera* a. Extraction of Proteoglycan from *Microciona prolifera*

Fresh marine sponges (*Microciona prolifera*) collected from the Cape Cod area (USA) are rinsed with 0.5M NaCl, 0.18 g/l NaHCO$_3$, (buffer A) and cut into cubes 1×1 cm. The cubes are incubated in the buffer A (50% suspension) for 12 h at +4°C under gentle rotation. After filtration of the sponge cubes suspension through cheese cloth, the cubes were two more times extracted with the buffer A using the same incubation conditions. The supernatants are either combined or separately centrifuged at 3000×g for 30 min at +4°C, and the obtained supernatant is again centrifuged at 12,000×g for 40 min at +4°C. CaCl$_2$, is added to the supernatant to a concentration of 20 mM. After 2-12 h gentle shaking at room temperature, the precipitated proteoglycan is centrifuged at 3000×g for 20 min at room temperature. The pelleted proteoglycan is dissolved in at lest 20 volumes of 0.5 M NaCl, 2 mM CaCl$_2$, 20 mM Tris pH 7.4 (buffer B) and centrifuged at 10,000×g for 30 min at +4°C to remove insoluble material. Supernatant was centrifuged at 100,000×g for 4 h at +40 C, and the pelleted proteoglycan redissolved in buffer B at concentration of 1-2 mg/ml. To the dissolved proteoglycan in buffer B solid CsCl$_2$ is added to make a 50% concentration, and the solution is centrifuged in a SW rotor at 100,000×g for 36 h at room temperature. The pelleted proteoglycan is dialyzed against buffer B and stored at +4°C in the presence of 0.05% NaN$_3$.

The purified proteoglycan thus obtained exhibits the following characteristics:

1) Molecular mass: 19,000 kD 0.20%.
2) Sedimentation coefficient S$_{20w}$: 58 20%.
3) Stability to enzymes: Not digestible with Chondroitinase A, B, C, Heparinase, Heparitinase, Hyaluronidase and Keratinase.
4) Gelation: Forms gel in aqueous salt solution containing more then 6 mM CaCl$_2$ or in deionized water.
5) Shape determined with atomic force microscopy in liquid and electron microscopy: circle of 400-500 nm diameter with 10-20 arms 200-300 nm long.
6) Stability: circle portion dissociates from arms in aqueous salt solutions containing less then 1 mM CaCl$_2$; or in the presence of EDTA.
7) Ca$^{2+}$ binding determined by flame ionization spectrometry: binds ca. 7000 moles of Ca$^{2+}$/mole of proteoglycan at 2 mM CaCl$_2$ and ca. 70,000 moles of Ca$^{2+}$/mole of proteoglycan at 20 mM CaCl$_2$.
8) Dissociation fingerprinting: Dissociation of proteoglycan by 1% SDS at 100°C gave nine fragments ranging from 38-1500 kD on a 5-20% linear gradient polyacrylamide gel after electrophoresis. These fragments had apparent molecular masses of ca. 1500 kD, 500 kD, 250 kD, 150 kD, 148 kD, 135 kD, 108 kD, 70 kD, and 38 kD. EDTA and heating at 80°C produced fragments of Mr 1500×10$^3$, 250×10$^3$ on gel filtration chromatography. Trypsin digestion produced fragments of Mr 124×10$^3$, 70×10$^3$, 27×10, 10×10$^3$ gel filtration chromatography.

Table I shows approximate amino acid (measured by HPLC pico-tag) and approximate total sugar composition (measured by gas chromatography after methanolysis, reacetylation and silylation):

This proteoglycan consists of approximatively 36% by weight proteins and 64% by weight carbohydrates.

TABLE I

| Intact proteoglycan (PG) | (mol %) | Isolated glycans | (mol %) |
|---|---|---|---|
| mol amino acid/mol PG | | mol amino acid/mol glycan | |
| Asx | 12,736 | 13.4 | 1.2 | 33.4 |
| Thr | 8,196 | 8.6 | 0.6 | 16.7 |
| Ser | 6,179 | 6.7 | 0.3 | 8.4 |
| Glx | 11,475 | 12.0 | 0.7 | 19.5 |
| Pro | 5,611 | 6.0 | 0.0 | 0.0 |
| Gly | 12,484 | 13.1 | 0.5 | 13.8 |
| Ala | 9,205 | 9.7 | 0.1 | 2.8 |
| Val | 5,296 | 5.8 | 0.0 | 0.0 |
| Met | 693 | 0.8 | 0.0 | 0.0 |
| Ile | 3,287 | 4.5 | 0.0 | 0.0 |
| Leu | 6,997 | 7.4 | 0.1 | 2.7 |
| Tyr | 3,972 | 4.2 | 0.0 | 0.0 |
| Phe | 3,530 | 3.7 | 0.1 | 2.7 |

TABLE I-continued

| Intact proteoglycan (PG) | (mol %) | Isolated glycans | (mol %) |
|---|---|---|---|
| His | 945 | 1.0 | 0.0 | 0.0 |
| Lys | 1,261 | 1.3 | 0.0 | 0.0 |
| Arg | 1,765 | 1.8 | 0.0 | 0.0 |
| Total | 94,629 | 100% | 3.6 | 100% |
| mol carbohydrate/mol PG | | mol carbohydrate/mol glycan | |
| Fuc | 15,069 | 33.9 | 9.9 | 34.7 |
| GlcUA | 4,602 | 10.3 | 2.0 | 7.2 |
| Man | 4,035 | 9.1 | 2.7 | 9.6 |
| Gal | 10,907 | 24.5 | 7.4 | 26.1 |
| GlcNAc | 9,836 | 22.2 | 6.3 | 22.3 |
| Total | 44,449 | 100.0 | 28.3 | 100 |
| mol/mol PG | | | |
| SO$_4^{2-}$ | 8,241 | | | |

Standard deviation is less then 20% of each value. Asx signifies Asn or Asp; Glx signifies Glu or Gln. It is also noted that apparant amounts of Ile and Leu are somewhat variable depending on the preparation. The amount of uronic acid determined colormetrically is usually 2 times higher then the amount determined by gas chromatography. SO$_4^{2-}$ was determined by HPLC ion chromatography after hydrolysis of PG.

The N-terminal sequence of the backbone of the molecule is as follows:

```
Seq. I      Pro-Leu-Phe-Thr-Val-Pro-Ile-Tyr-Val-Pro-
            Glu-Asp-Gln-Leu

Seq. II     Pro-Glu-Val-Gly-Val-Pro-Ile-Tyr-Val-Pro-
            Glu-Asp-Gln-Leu

Seq. III    Pro-Val-Val-Gly-Val-Pro-Ile-Tyr-Val-Pro-
            Glu-Asp-Gln-Leu.
            preferably Sequence 1.
```

Seq. I-Seq. III correspond to SEQ ID NOS 1-3 respectively.

Trypsin digestion of the molecule provides peptides having the sequences:

```
Seq. IV     Phe-Val-Val-Met-Arg

Seq. V      Pro-Gln-Asp-Pro-Phe

Seq. VI     Leu-Ala-Gly-Val-Val-Ile

Seq. VII    Pro-Gln-Ala-Ser-Ser-Gly

Seq. VIII   Ala-Ala-Gln-Trp-Ile-Gly-Gln-Lys
```

Seq. IV-Seq. VIII correspond to SEQ ID NOS 4-8 respectively.

b. Isolation of Acidic Glycans from the *Microciona prolifera* Proteoglycan

Frozen proteoglycan as obtained above is extracted with water/methanol/chloroform 3/8/4 V/V/V, and the nonlipid fraction, was pelleted by centrifugation at 4000×g for 15 min at +4° C. This extraction is repeated and the pellet is dried under a vacuum. The pellet is wetted in ethanol and resuspended in 0.1 M Tris pH 8, 1 mM CaCl$_2$ and 100-200 μg Pronase (Calbiochem) (preincubated for 30 min at 60° C. in 0.1M Tris pH 8, 1 mM CaCl$_2$ per 1-2 mg dried powder material), and the pellet is digested at 60° C. for three days. Two more equivalent portions of preincubated pronase are added at 24 h intervals. DNAse I is then added (30 μg) and incubation is continued at 37°C in the presence of 10 mM MgCl$_2$. The digested sample is then treated again with pronase and chromatographed through G-25 Sephadex (Pharmacia) column eluted with 10 mM pyridine acetate pH 5, void volume fractions are collected and lyophilized, and the glycans thus obtained are dissolved in 50 mM NaOH in the presence of 1M NaHBO$_4$ and incubated at 45° C. for 16 h (NaOH treatment may also be omitted). The glycans are passed through Dowex AG 50W-X8 column in H+ form (Bio-Rad) eluted with water, nonbound glycans are immediately neutralized and electrophoresed on a 5-20% or 10-40% linear polyacrylamide gradient gels (Tris/borate-EDTA), and separated acidic glycans of Mr 200×10$^3$ are eluted from gels. (Optionally, the acidic glycans can be sepatated by gel filtration rather than electrophoresis). The isolated acidic glycan molecules are desalted using P-2 column (Bio-Rad) eluted with 10 mM pyridine acetate pH 5, lyophilized and stored at −20° C.

The acidic glycan fraction is comprised of two major glycans of apparent molecular mass determined by gel electrophoresis using glycosaminoglycan standards of ca. 200 kD and 6 kD. The glycans have the following molar composition (expressed as moles of monosaccharide units/mole of glycan), as determined by gas chromatography, as shown in Table II:

TABLE II

| | 200 kD glycan | 6 kD glycan |
|---|---|---|
| Fuc | 680 | 3 |
| Man | 20 | 2 |
| Gal | 180 | 5 |
| GlcNAc | 190 | 14 |
| GlcUA | 320 | 7 |
| Asn | 1 | 1 |

Standard deviation is less then 20% of each value. Per mole of proteoglycan, there are 20 moles of the 200 kD glycan and 1000 moles of the 6 kD glycan. The glycans are not digestible with Chondroitinase A, B, C, Heparinase, Heparitinase, Hyaluronidase or Keratinase. They are soluble in aqueous solutions and do not form gels in 6 mM CaCl$_2$, salt solutions. At higher concentrations, e.g. >1 mg/ml water, they will undergo hydrolysis at room temperature.

After partial acid hydrolysis of isolated glycans fragments were purified by ion exchange chromatography and high performance liquid chromatography. Methylation analysis, sequential enzymatic and chemical degradation, $^1$H-NMR spectroscopy, fast atom bombardment-mass spectrometry, ion spray mass-spectrometry and MALDI-TOF of nine purified fragments showed following oligosaccharide structures:

Structure 1
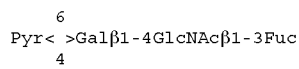
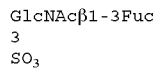

is repeated 1000 times per mole proteoglycan.

Structure 2
    GlcNAcβ1-3Fuc
    3
    SO$_3$ is repeated 2000 times per mole proteoglycan.

Structure 3
    Galα1-2Galβ1-4GlcNAcβ1-3Fuc
    3
    SO$_3$ is repeated 2000 times per mole proteoglycan.

Structure 4
(SO$_3$)GlcNAc-Fuc-Fuc:

Structure 5
Fuc-(SO$_3$)GlcNAc-Fuc

Structure 6
GlcNAc-(SO$_3$)Gal-Fuc

Structure 7
Gal-(SO$_3$)Gal-GlcNAc-Fuc-Fuc

Structure 8
Gal-(SO$_3$)Gal-GlcNAc-Fuc-Fuc

Structure 9
GlcNAc-Fuc-(SO$_3$)Gal-Fuc

EXAMPLE 2

Preparation of Proteoglycans and Acidic Glycans from *Halichondria panacea*

Extraction of proteoglycan from Hatichondria panicea and isolation of acidic glycans from *Halichondria panicea* proteoglycan is performed as described in example 1 for *Microciona prolifera*. The proteoglycan thus obtained has the following characteristics:

0.1) Molecular mass: 10,000 kD 20%.
2) Sedimentation coefficient of S$_{20w}$ 42 20%.
4) Stability to enzymes: Not digestible with Chondroitinase A, B, C, Heparinase, Heparitinase, Hyaluronidase and Keratinase.
5) Gelation: Forms gel in aqueous salt solution containing more then 6 mM CaCl$_2$ or in deionized water.

This proteoglycan consists of approximately 79% protein and 21% carbohydrate by weight. It has an approximate amino acid composition (as measured by HPLC pico-tag) and approximate total sugar composition (as measured by gas chromatography) as shown in Table III:

TABLE III

Amino acid composition, and carbohydrate composition Intact proteoglycan (PG)

| Amino acid | (mol %) |
|---|---|
| Asx | 9.1 |
| Glx | 9.2 |
| Ser | 7.0 |
| Gly | 9.9 |
| Arg | 7.6 |
| Thr | 10.2 |
| Ala | 7.0 |
| Pro | 8.2 |
| Tyr | 4.6 |
| Val | 8.6 |
| Met | 2.5 |

TABLE III-continued

Amino acid composition, and carbohydrate composition
Intact proteoglycan (PG)

| | |
|---|---|
| Cys | 0.1 |
| Ile | 6.0 |
| Leu | 5.5 |
| Phe | 4.8 |
| Total Carbohydrate | 100% |
| Fuc | 12.5 |
| Xyl | 1.9 |
| GlcUA | 3.2 |
| GalUA | 1.7 |
| Man | 16.7 |
| Gal | 36.2 |
| Glc | 13.6 |
| GlcNAc | 14.2 |
| Total | 100.0 mol/mol PG |
| $SO_4^{2-}$ | 6,250 |

Standard deviation is less then 20% of each value. Asx signifies Asn or Asp; Glx signifies Glu or Gln. It is also noted that apparant amounts of Ile and Leu are somewhat variable depending on the preparation. The amount of uronic acid determined colorimetrically is usually 2 times higher then the amount determined by gas chromatography. $SO_4^{2-}$ was determined by HPLC ion chromatography after hydrolysis of PG.

Isolation of acidic glycans from this proteoglycan in the manner described in example I gives seven glycans having apparent molecular mass determined by gel electrophoresis using glycosaminoglycan standards of ca.>1000 kD, 600 kD, 160 kD, 150 kD, 110 kD, 82. kD, and 50 kD.

After partial acid hydrolysis of isolated glycans fragments were purified by ion exchange chromatography and high performance liquid chromatography. Methylation analysis, sequential enzymatic and chemical degradation, $^1$H-NMR spectroscopy, fast atom bombardment-mass spectrometry, ion spray mass-spectrometry and MALDI-TOF of eight purified fragments showed following oligosaccharide structures:

```
structure 10
Pyr(4,6)Gal-Gal-Fuc structure 11
Pyr(4,6)Gal-Gal-Fuc-GlcNAc structure 12
Pyr(4,6)Gal-Fuc
         Gal structure 13
Pyr(4,6)Gal-GlcNAc-Fuc
         Gal structure 14
Pyr(4,6)Gal-GlcNAc-Fuc
              Gal structure 15
Pyr(4,6)Gal-Gal-GlcNAc-Fuc
         Gal structure 16
Pyr(4,6)Gal-Gal-GlcNAc-Fuc
         Pyr(4,6)Gal structure 17
Pyr(4,6)Gal-Gal-Gal-GlcNAc-Fuc
         Pyr(4,6)Gal
```

EXAMPLE 3

Preparation of Proteoglycans and Acidic Glycans from *Mycale lingua*

Extraction of proteoglycan from *Mycale lingua* and isolation of acidic glycans from *Mycale lingua* proteoglycan is performed as described in example 1 for *Microciona prolifera*. The proteoglycan thus obtained has the following characteristics:

1) Molecular mass: 12,000 kD 20%.
2). Sedimentation coefficient of $S_{20,W}$ 48 20%.
4) Stability to enzymes: Not digestible with Chondroitinase A, B, C, Heparinase, Heparitinase, Hyaluronidase and Keratinase.
5) Gelation: Forms gel in aqueous salt solution containing more then 6 mM $CaCl_2$; or in deionized water.

This proteoglycan consists of approximately 58% protein and 42% carbohydrate by weight. It has an approximate amino acid composition (as measured by HPLC pico-tag) and approximate total sugar composition (as measured by gas chromatography) as shown in Table IV:

TABLE IV

Amino acid composition and carbohydrate composition
Intact proteoglycan (PG)

| | (mol %) |
|---|---|
| amino acid | |
| Asx | 10.8 |
| Glx | 9.6 |
| Ser | 6.3 |
| Gly | 7.7 |
| Arg | 9.5 |
| Thr | 10.9 |
| Ala | 8.0 |
| Pro | 7.9 |
| Tyr | 0.5 |
| Val | 9.0 |
| Met | 1.8 |
| Cys | 0.2 |
| Ile | 6.2 |
| Leu | 6.0 |
| Phe | 5.6 |
| Total carbohydrate | 100.0 |
| Fuc | 29.7 |
| Xyl | 1.0 |
| GlcUA | 11.5 |
| GalUA | 0.8 |
| Man | 11.0 |
| Gal | 15.3 |
| Glc | 16.7 |
| GalNAc | 6.3 |
| GlcNAc | 7.7 |
| Total | 100.0 mol/mol PG |
| $SO_4^{2-}$ | 12,000 |

Standard deviation is less then 20% of each value. Asx signifies Asn or Asp; Glx signifies Glu or Gln. It is also noted that apparant amounts of Ile and Leu are somewhat variable depending on the preparation. The amount of uronic acid determined colormetrically is usually 2 times higher then the amount determined by gas chromatography. $SO_4^{2-}$ was determined by HPLC ion chromatography after hydrolysis of PG.

EXAMPLE 4

Preparation of Proteoglycans and Acidic Glycans from *Cliona celata*

Extraction of two proteoglycans from *Cliona celata* and isolation-of acidic glycans from *Cliona celata* proteoglycans is performed as described in example 1 for *Microciona prolifera* with the exception that precipitation with $CaCl_2$, could be omitted. Two proteoglycan designated CPGI (more abundant in the first extraction) and CPG2 (more abundant in the second extraction) thus obtained has the following characteristics:

1) Molecular mass: CPGI>20,000 kD 20%; CPG2 6,000 kD.
2) Sedimentation coefficient of CPGI $S_{20W}$ 125 20%; CPG2 26 $S_{20W}$ 20%.
4) Stability to enzymes: Not digestible with Chondroitinase A, B, C, Heparinase, Heparitinase, Hyaluronidase and Keratinase.
5) Gelation: Both protegylcans form viscous gels in aqueous salt solution containing more then 6 mM $CaCl_2$; or in deionized water.

CPGI consists of approximately 26% protein and 74% carbohydrate by weight (determined colorimetrically). CPG2 consists of approximately 32% protein and 68% carbohydrate by weight. They have an approximate amino acid composition (as measured by HPLC pico-tag) and approximate total sugar composition (as measured by gas chromatography) as shown in Table V:

TABLE V

Amino acid composition and carbohydrate composition

| | Intact proteoglycan | |
|---|---|---|
| | (CPG1) | (CPG2) |
| | (mol %) | (mol %) |
| amino acid | | |
| Asx | 1.0 | 7.8 |
| Glx | 5.6 | 9.5 |
| Ser | 7.1 | 11.3 |
| Gly | 10.6 | 10.9 |
| Arg | 23.6 | 6.0 |
| Thr | 18.1 | 14.1 |
| Ala | 0.7 | 7.7 |
| Pro | 12.9 | 10.7 |
| Tyr | 8.3 | 0.7 |
| Val | 1.9 | 6.1 |
| Met | 2.4 | 2.4 |
| Cys | 0.3 | 0.2 |
| Ile | 1.0 | 3.9 |
| Leu | 1.3 | 5.1 |
| Phe | 0.8 | 3.6 |
| Lys | 4.3 | 0.1 |
| Total carbohydrate | 100.0 | |
| Fuc | 11.0 | 17.8 |
| Xyl | 2.2 | 2.2 |
| GlcUA | 9.4 | 11.0 |
| GalUA | 0.7 | 1.1 |

TABLE V-continued

Amino acid composition and carbohydrate composition

| | Intact proteoglycan | |
|---|---|---|
| | (CPG1) | (CPG2) |
| Man | 1.2 | 5.9 |
| Gal | 6.8 | 12.8 |
| Glc | 17.2 | 18.5 |
| GalNAc | 32.5 | 16.2 |
| GlcNAc | 19.0 | 14.8 |
| Total | 100.0 | |
| | mol/mol PG | mol/mol PG |
| $SO_4^{2-}$ | 12,000 | 6,000 |

Standard deviation is less then 20% of each value. Asx signifies Asn or Asp; Glx signifies Glu or Gin. It is also noted that apparant amounts of Ile and Leu are somewhat variable depending on the preparation. The amount of uronic acid determined colorimetrically is usually 2 times higher then the amount determined by gas chromatography. $SO_4^{2-}$ was determined by HPLC ion chromatography after hydrolysis of PG.

Proteoglycans purified from *Cliona celata* using the same procedure as in Example 1. Calcium chlorid precipitation was preformed during purification.

| | |
|---|---|
| $M_r \times 8\,10^6$ | |
| $s_{20,w}$ (S) 46 | |
| Carbohydrate/protein ratio (w/w) | 36/64 |

TABLE VB

| Aminoacid composition (mol %) | |
|---|---|
| Asx | 7.8 |
| Glx | 9.5 |
| Ser | 11.3 |
| Gly | 10.9 |
| Arg | 6.0 |
| Thr | 14.1 |
| Ala | 7.7 |
| Pro | 10.7 |
| Tyr | 0.7 |
| Val | 6.1 |
| Met | 2.4 |
| Cys | 0.2 |
| Ile | 3.9 |
| Leu | 5.1 |
| Phe | 3.6 |
| Lys | 0.1 |
| Carbohydrate composition (mol %) | |
| Ara | 9.4 |
| Fuc | 22.9 |
| Xyl | 1.5 |
| GlcUA | 6.4 |
| GalUA | N.D. |
| Man | 12.9 |
| Gal | 11.3 |
| Glc | 4.6 |
| GalNAc | 9.2 |
| GlcNAc | 22.0 |
| $SO_4^{2-}$ (mol/mol) | 7000 |

Standard deviation is less then 20% of each value. Asx signifies Asn or Asp; Glx signifies Glu or Gin. It is also noted that apparant amounts of Ile and Leu are somewhat variable depending on the preparation. The amount of uronic acid determined calorimetrically is usually 2 times higher then the amount determined by gas chromatography. $SO_4^{2-}$ was determined by HPLC ion chromatography after hydrolysis of PG.

N.D.=Not Detected.

After partial acid hydrolysis of isolated glycans fragments were purified by ion exchange chromatography and high performance liquid chromatography. Methylation analysis, sequential enzymatic and chemical degradation, $^1$H-NMR spectroscopy, fast atom bombardment-mass spectrometry, ion spray mass-spectrometry and MALDI-TOF of 16 purified fragments showed following oligosaccharide structures:

```
structure 18
Gal-GlcNAc-Fuc(SO3)-GlcNAc-Fuc structure 19
Gal-GlcNAc-Ara(SO3)-GlcNAc-Fuc structure 20
Gal-GalNAc-Fuc(SO3)-GlcNAc-Fuc structure 21
Gal-GalNAc-Fuc(SO3)-GalNAc-Fuc structure 22
Gal-GlcNAc-Fuc(SO3)-GalNAc-Fuc structure 23
Gal-GalNAc-Ara(SO3)-GlcNAc-Fuc structure 24
Gal-GalNAc-Ara(SO3)-GalNAc-Fuc structure 25
Gal-GlcNAc-Ara(SO3)-GalNAc-Fuc structure 26
GlcNAc-Fuc(SO3)-GlcNAc-Fuc-Fuc structure 27
GlcNAc-Ara(SO3)-GlcNAc-Fuc-Fuc structure 28
GalNAc-Fuc(SO3)-GlcNAc-Fuc-Fuc structure 29
GalNAc-Fuc(SO3)-GalNAc-Fuc-Fuc structure 30
GlcNAc-Fuc(SO3)-GalNAc-Fuc-Fuc structure 31
GalNAc-Ara(SO3)-GlcNAc-Fuc-Fuc structure 32
GalNAc-Ara(SO3)-GalNAc-Fuc-Fuc structure 33
GlcNAc-Ara(SO3)-GalNAc-Fuc-Fuc
```

EXAMPLE 5

Preparation of Acidic Glycans from *Lytechinus pictius*

*Lytechinus pictus* sea urchin eggs and/or embryos (from 2 cell stage to plutes stage) were washed with sterile sea water and pelleted embryos were extracted with water/methanol/chloroform. 3/8/4 V/V/V, and the nonlipid fraction was pelleted by centrifugation at 4000×g for 15 min at +4° C. This extraction is repeated and the pellet is dried under a vacuum. The pellet is wetted in ethanol and resuspended in 0.1 M Tris pH 8, 1 mM $CaCl_2$; and 100-200 μg Pronase (Calbiochem) (preincubated for 30 min. at 60° C. in 0.1M Tris pH 8, 1 mM $CaCl_2$, per 1-2 mg dried powder material), and the pellet is digested at 60° C. for three days. Two more equivalent portions of preincubated pronase are added at 24 h. intervals DNAse I is then added (30 μg) and incubation is continued at 37° C. in the presence of 10 mM $MgCl_2$. The digested sample is then treated again with pronase and chromatographed through G-25 Sephadex (Pharmacia) column eluted with 10 mM pyridine acetate pH 5, void volume fractions are collected and lyophilized, and the glycans thus obtained are dissolved in 50 mM NaOH in the presence of 1M $NaHBO_4$ and incubated at 45° C. for 16 h (NaOH treatment may also be omitted). The glycans are passed through Dowex AG 50W-X8 column in H+ form (Bio-Rad) eluted with water, nonbound glycans are immediately neutralized and electrophoresed on a 5-20% or 10-40% linear polyacrylamide gradient gels (Tris/borate-EDTA), and separated acidic glycans of Mr 200×10' are eluted from gels. (Optionally, the acidic glycans can be sepatated by gel filtration rather than electrophoresis). The isolated acidic glycan molecules are desalted using P-2 column (Bio-Rad) eluted with 10 mM pyridine acetate pH 5, lyophilized and purified by affinity chromatography with the Block 2 monoclonal antibodies of ref Misevic et al. mentioned above stored at −20° C.

1) Molecular mass: 580 kD 20%.

2) Sedimentation coefficient 8.5 $S_{20w}$ 20%.

4) Stability to enzymes: Not digestible with Chondroitinase A, B, C, Heparinase, Heparitinase, Hyaluronidase and Keratinase.

5) Gelation: self-interacton-oligomerization in aqueous salt solution containing more then 6 mM $CaCl_2$ or in deionized water.

TABLE VI

| | | (mol. %) |
|---|---|---|
| mol carbohydrate/molacidic glycan | | |
| Fuc | 737 | 25.40 |
| Xyl | 108 | 3.73 |
| Gal | 39 | 1.34 |
| Glc | 12 | 0.41 |
| GlcUA | 786 | 27.10 |
| GalNAc | 506 | 17.46 |
| GlcNAc | 712 | 24.56 |
| Total | 2,900 | 100.0 |
| | mol/mol | |
| $SO_4^{2-}$ | 1,600 | |

Standard deviation is less then 20% of each value. The amount of uronic acid determined colormetrically is usually 2 times higher then the amount determined by gas chromatoaraphy. $SO_4^{2-}$ was determined by HPLC ion chromatography after hydrolysis of PG.

EXAMPLE 6

Ex Vivo Stimulation of Human NK Cells Proliferation by *Microciona prolifera* Proteoglycan and by Its Acidic Glycans Human peripheral blood mononuclear cell (PBMC) are isolated from 10 ml of blood by centrifugation on Ficoll gradient (Pharmacia). Stimulation of PBMC proliferation with 100 μg/ml acidic glycans or proteoglycans is performed in the presence of complete medium (RPMI 1640, 5% human AB serum, 2 mM L-Glutamine, 1 mM Na pyruvate, non-essential amino acids and 50 μg/ml Kanamycin). After 5 days 5 U/ml of human recombinant IL-2 is added. One half of medium is changed when it becomes acidic. After 7, 14, 21, 28 and 35 days cells were analyzed by FACS using antibodies against following markers: CD3, TCR αβ, TCR γδ, CD4, CD8-T cells; CD 16, CD56-NK cells; CD20-B cell; CD14 monocytes. Results from five different donors after 3 weeks. In the PBMC cultures treated with acidic glycans, NK cells population (CD 16 and CD 56 positive) and (CD3, TCR αβ, TCR γδ, CD4, CD8, CD20 and CD 14 negative) increased from 1-5% to 30-80% of the total PBMC, whereas untreated controls remained at a level of 1-5% NK cells. Specific stimulation of NK cells proliferation by glycans was confirmed by $^3$H thymidine incorporation only in isolated clones of NK cells and not of αβT cells isolated from the same PBMC cultures.

EXAMPLE 7

Ex-Vivo Stimulation of Human NK Cells Proliferation by *Mycale lingua* and *Cliona celata* Proteoglycans and by Their Acidic Glycans was Similar to *Microciona prolifera* Proteoglycan The data for example 6 above is applicable hereto.

EXAMPLE 8

Ex Vivo Stimulation of Human NK Cells Proliferation by *Lytechinus pictus* Acidic Glycan with 580 kD was Similar to *Microciona prolifera* Proteoglycan The data for example 6 above is applicable hereto.

EXAMPLE 9

Stimulation of Human γδT Cells Proliferation (Ex Vivo) by *Microciona prolifera* Proteoglycan, *Halichondria panacea* Proteoglycan and/or Their Acidic Glycans Same culturing procedure as described in the previous example shows that *Microciona prolifera* acidic glycans stimulate only one subpopulation of γδT cells via T cell receptor with an increase from 5% to 20%. *Halichondria panicea* proteoglycan and its acidic glycans stimulate a different population of γδT cells from 5% to 70%. These data are confirmed by 3H thymidine incorporation in isolated clones stimulated by specific acidic glycans.

EXAMPLE 10

Anti-tumorogenic and Anti-metastatic Activity of Proteoglycans and Their Acidic Glycans from *Microciona prolifera* (In Vivo)

Seven C-57 black mice are injected i.p. with 300 μg proteoglycan or acidic glycans from *Microciona prolifera*/200 μl 0.2M NaCl, 2 mM CaCl$_2$, 20 mM Tris pH 7.4/animal, every day for five days. At day five, animals are injected with 2.5×10$^4$ B-16 melanoma cells per animal. Animals are immunized for five more days with proteoglycan as described above. The appearance of tumor, tumor growth, survival of animals and appearance of metastasis are observed in immunized animals and compared with control animals injected with buffer. Control animals which have not received proteoglycan all exhibit marked melanoma growth followed by metastasis. Compared to controls, treated animals exhibit a 20% delay in the time of appearance and 50% reduction in growth of syngenic B16 melanomas, a 12% increase in the total time of survival of all immunized mice (p=0.0044), and complete inhibition of metastasis.

EXAMPLE 11

Anti-tumorogenic and Anti-metastatic Activity of Proteoglycans and Their Acidic Glycans from *Halichondria panicea, Mycale lingua, Cliona celata* and *Lytechinus pictus*

The proteoglycans or acidic glycans obtained from *Halicohondria panicea, Mycale lingua, Cliona celata* and *Lytechinus pictus* were tested separately in C-57 black mice in accordance with the protocol described in example 10. The appearance of tumor, tumor growth, survival of animals and appearance of metastasis are observed in immunized animals and compared with control animals injected with buffer. Control animals which have not received proteoglycan all exhibit marked melanoma growth followed by metastasis. Compared to the controls, the treated animals exhibited a delay in the time of appearance and a reduction in growth of syngenic B16 melanomas, an increase in the survival time and an inhibition of metastasis which was similar to that achieved with the proteoglycan used in example 10.

EXAMPLE 12

Cloning and Expression of Gene for Proteoglicans from *Microciona prolifera*

Proteoglycan (PG) cDNA is isolated from a random-primed cDNA library created using poly(A)+RNA from *Microciona prolifera* cells. This cDNA library is screened using the N-terminal amino acid sequence of PG described in example I above by colony hybridization techniques, i.e., expressing the library in an expression system, preferably *E. coli*, lysing the colonies, e.g., on nitrocellulose filters, denaturing their DNA in situ and fixing it on the filter, hybridizing with labeled, preferably radiolabeled, oligonucleotide probes of at least 30 base pairs having cDNA base sequences corresponding to all or a portion of the N-terminal sequence of PG, identifying hybridized colonies, and retrieving the corresponding vectors from the library, using chromosome walking techniques if necessary to isolate and characterize one or more cDNA fragments containing one or more regions coding for glycosylation sites for N-linked glycans. (Note that the cDNA is repetitive, so it is not necessary to clone, isolate and characterize the entire sequence). Once the desired portion of cDNA has been isolated, it is expressed in a suitable expression system, preferably a eukaryotic system, most preferably a sponge. The PG is isolated from the sponge or from the culture medium of the expression system, e.g., using the procedures outlined above.

EXAMPLE 13

Therapeutic Anti-tumoreognic and Anti-metastatic Activity of Proteoglycans and Their Acidic Glycans from *Microciona prolifera, Halichondria panicea, Mycale lingua, Cliona celata* and *Lytechinus pictus* (In Vivo) Injected in Pharmaceutically Acceptable Diluents and No Therapeutical Effects when Proteoglycans were Injected in Pharmaceutically Not Acceptable Hypotonic or Hypertonic Diluents Containing Freunds Adjuvant Forty C-57 black mice were injected with $2.5 \times 10^4$ B-16 melanoma cells in leg per animal. After one day animals were injected i.p. or intra tumor five times with 150 µg proteoglycans or acidic glycans from *Microciona prolifera* (eight animals), *Halichondria panicea* (eight animals), *Mycale lingua* (eight animals), *Cliona celata* (eight animals), and *Lytechinus pictus* (eight animals)/200 µl 0.188NaCl, 1 mM $CaCl_2$ 10 mM Tris pH 7.4/animal, with first three injections given in interval of 3 days and last two injections in interval of 7 days. The appearance of tumor, tumor growth, survival of animals and appearance of metastasis were compared with control not proteoglycan treated animals and animals treated with pharmaceutically not acceptable diluents:
1) hypotonic injection of 200 kg proteoglycans/300 µg water with complete Freunds adjuvant and
2) hypertonic injection of 200 µg proteoglycan/300 µl 0.5 M NaCl, 2 mM $CaCl_2$, 20 mM Tris pH 7.4 or bicarbonate (CSW) with complete Freunds Adjuvant.

Control animals and animals which received therapy with pharmaceutically not acceptable diluents of hypotonic and hypertonic proteoglycan with Complete Freunds adjuvant all exhibit marked melanoma growth followed by metastasis. In same cases animals treated with pharmaceutically not acceptable diluents of hypotonic and hypertonic proteoglycan with Complete Freunds adjuvant were more ill and had reduced life span under the melanoma bourdon when compared to controls. Animals treated with proteoglycans in pharmaceutically acceptable diluents in comparison with the control not treated animals exhibited a 20%-30% delay in time of tumor appearance, 50%-80% reduction in growth of syngenic B16 melanoma tumors, a 12%-20% increase in the total time of survival ($p_{max}$=0.004), and absence of visible B16 melanoma metastasis.

EXAMPLE 14

Anti-tumoreognic and Anti-metastatic Vaccine Activity of Proteoglycans and Their Acidic Glycans from *Microciona prolifer, Halichondria panicea, Mycale lingua, Cliona celata* and *Lytechinus piclus* (In Vivo) Injected in Pharmaceutically Acceptable Diluents and No Therapeutical Effects when Proteoglycans and their Acidic Glycans were Injected in Pharmaceutically Not Acceptable Hypotonic or Hypertonic Diluents Containing Freunds Adjuvant Fifty C-57 black mice were injected i.p. or intra tumor five times with 150 µg proteoglycans or acidic glycans of *Microciona prolifera*, (ten animals) *Halichondria panicea*, (ten animals), *Mycale lingua* (ten animals), *Cliona celata* (ten animals) and *Lytechinus pictus* (ten animals)/200 µl 0.188NaCl, 1 mM $CaCl_2$ 10 mM Tris pH 7.4/animal, with first three injections given in interval of 3 days and last two injections in interval of 7 days. One day after last proteoglycan injection $2.5 \times 10^4$ B-16 melanoma cells were injected in leg per animal. The appearance of tumor, tumor growth, survival of animals and appearance of metastasis were compared with control not proteoglycan treated animals and animals treated with pharmaceutically not acceptable diluents:
1) hypotonic injection of 200 µg proteoglycans/300 µg double distilled water with complete Freunds adjuvant and
2) hypertonic injection of 200 µg proteoglycan/300 µg 0.5 M NaCl, 2 mM $CaCl_2$, 20 mM Tris pH 7.4 with complete Freunds Adjuvant.

Control animals and animals which received vaccine with pharmaceutically not acceptable diluents of hypotonic and hypertonic proteoglycan with Complete Freunds adjuvant all exhibit marked melanoma growth followed by metastasis. In same cases animals treated with pharmaceutically not acceptable diluents of hypotonic and hypertonic proteoglycan with Complete Freunds adjuvant were more ill and had reduced life span under the melanoma burden when compared to controls. Animals treated with proteoglycans vaccine in pharmaceutically acceptable diluents in comparison with the control not treated animals exhibited a 20% delay in time of tumor appearance, 50% reduction in growth of syngenic B16 melanoma tumors, a 12%-20% increase in the total time of survival (pmax 0.004), and absence of visible B16 melanoma metastasis.

EXAMPLE 15

Ex Vivo Stimulation of Human NK Cells Proliferation by *Microciona prolifera, Halichondria panicea Mycale lingua, Cliona celata*, and *Lytechinus pictus* Proteoglycans and by Their Acidic Glycans Attached to Tissue Culture Dishes Tissue culture dishes were coated separately by adsorption or cross linking to tissue culture dishes using 0.1 µg of proteoglycan or acidic glycan from *Microciona prolifera, Halichondria panicea Mycale lingua, Cliona celata* and *Lytechinus pictus* per 1 $cm^2$. After drying period of 30 min and UV sterilization dishes were washed three times with sterile phosphate buffered isotonic NaCl solution. Human peripheral blood mononuclear cells (PBMC) are isolated from 10 ml of blood by centrifugation on Ficoll gradient (Pharmacia). Isolated human PMBC were resuspended in 5% homologue human serum of the same donor in RPMI 1640 medium, 2 mM L glutamate, 1 mM Na-pyruvate and supplement of non-essential amino acids and 50 µg Kanamicine. Medium with homologue serum was change every 3-5 days. After 7, 14, 21 and 28 days cells were analyzed by immunofluorescence microscopy using following markers: CD3, TCR αβ, TCRγδ, CD4, CD8-T cells; CD CD16, CD56-NK cells; CD20 B cells; CD14 Monocytes. Within one week the population of NK (1-5% of the total cells) started to proliferate to reach 100% after three weeks.

EXAMPLE 16

Killing of Human Tumor Cells Ex Vivo with Human Nk Cells Proliferated on *Microciona prolifer, Halichondria panicea, Mycale lingua, Cliona celata* and *Lytechinus pictus* Proteoglycans and by Their Acidic Glycans Attached to Tissue Culture Dishes Tissue cultured human tumor cells lines were added in 1000 times excess to the number of human NK cells proliferated four weeks on *Microciona prolifera*, or *Halichondria panicea*, or *Mycale lingua*, or *Cliona celata* or *Lytechinus pictus* proteoglycans and/or its acidic glycans attached to tissue culture dishes. Massive and continuous killing of tumor cells coming in contact with NK cells is documented microscopically during the period of five weeks co culturing period.

In accordance with publications of the International Union of Pure and Applied Chemistry and International Union of Biochemistry and Molecular Biology, Joint Commission on Biochemical Nomenclature, Nomenclature of Carbohydrates (Recommendations 1996) published in Carbohydrate Research Volume 297 Number 1, Jan. 2, 1997, by Elsevier Science LTD, the linkage point of glycan fragments are at their respective reducing end with free aldehyde group, in our example fucose. Via this aldehyde group fragment can link to any respective hydroxyl group (glycosydic linkage) of the identical fragment and/or via inactive carrier to the next identical fragment to form repetitive linear or branched polymers.

EXAMPLE 17

Ex Vivo Stimulation of Human Nk Cells Proliferation, Anti-tumorogenic and Anti-metastatic Vaccine Activity, and Therapeutic Anti-tumoreognic and Anti-metastatic Activity by Fragments of Fucose-containing Acidic Glycans or Fucose-containing Proteoglycans from *Microciona prolifer, Halichondria panacea, Mycale lingua, Cliona celata* and *Lytechinus pictus*

Same procedures as described in the previous example show that fragments of fucose-containing acidic glycans or fucose-containing proteoglycans from *Microciona prolifer, Halichondria panicea, Mycale lingua, Cliona celata* and *Lytechinus pictus* have similar ex vivo stimulation of human NK cells proliferation, anti-tumorogenic and anti-metastatic vaccine activity, and therapeutic anti-tumoreognic and anti-metastatic activity.

Examples of several fragments structures obtained from fucose-containing acidic glycans, shown above structures 1 to 33, can have different degree and form of repetitiveness wherein linkages and points of attachments of repetitive structures are here schematically shown, e.g. each number in the schema is representing one monosaccharide of the fragment, dash (-) is linkage to the following monosaccharide within the fragment, and arrow (→) is linkage point between two fragments within the repetitive structure.

Example for trisaccharide sequence GlcNAc-Fuc-($SO_3$)Gal→GlcNAc-Fuc-($SO_3$)Gal is then 1-2-3→1-2-3. Based on this schematics below are presented different forms of repetitive structures, using this example structure, that can be implemented for each fragment structure of fucose-containing acidic glycan naturally obtained or obtained by chemical cross linking of the monomer fragment.

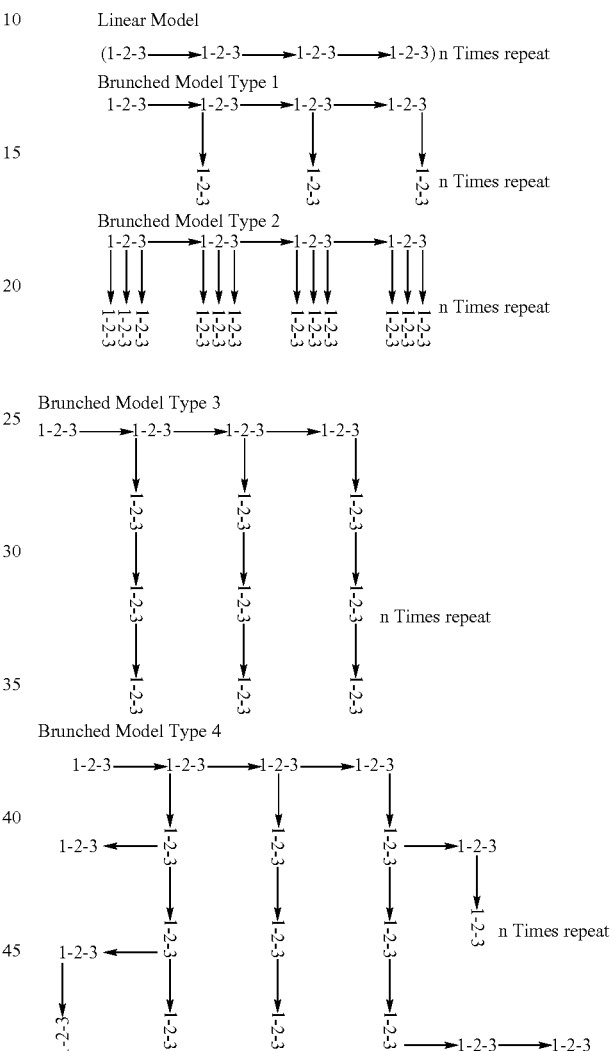

Besides this homo-type repetitive structures containing only one type of the fragment structure, also any hetero-type repetitive structure containing any combination of different types of fragments structures is possible.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

I claim:

1. An oligosaccharide of any of structures 1 to 33.

structure 1
$$\text{Pyr}< \begin{smallmatrix}6\\ \\4\end{smallmatrix} >\text{Gal}\beta 1\text{-}4\text{GlcNAc}\beta 1\text{-}3\text{Fuc}$$

structure 3
Galα1-2Galβ1-4GlcNAcβ1-3Fuc
3SO$_3$ structure 4
(SO$_3$)GlcNAc-Fuc-Fuc structure 5
Fuc-(SO$_3$)GlcNAc-Fuc structure 6
GlcNAc-(SO$_3$)Gal-Fuc structure 7
Gal-(SO$_3$)Gal-GlcNAc-Fuc-Fuc structure 8
Gal-(SO$_3$)Gal-GlcNAc-Fuc-Fuc structure 9
GlcNAc-Fuc-(SO$_3$)Gal-Fuc structure 10
Pyr(4,6)Gal-Gal-Fuc structure 11
Pyr(4,6)Gal-Gal-Fuc-GlcNAc structure 12
Pyr(4,6)Gal-Fuc
        Gal structure 13
Pyr(4,6)Gal-GlcNAc-Fuc
        Gal structure 14
Pyr(4,6)Gal-GlcNAc-Fuc
          Gal structure 15
Pyr(4,6)Gal-Gal-GlcNAc-Fuc
        Gal structure 16
Pyr(4,6)Gal-Gal-GlcNAc-Fuc
      Pyr(4,6)Gal structure 17
Pyr(4,6)Gal-Gal-Gal-GlcNAc-Fuc
    Pyr(4,6)Gal structure 18
Gal-GlcNAc-Fuc(SO$_3$)-GlcNAc-Fuc structure 19
Gal-GlcNAc-Ara(SO$_3$)-GlcNAc-Fuc structure 20
Gal-GalNAc-Fuc(SO$_3$)-GlcNAc-Fuc

```
structure 21
Gal-GalNAc-Fuc(SO3)-GalNAc-Fuc structure 22
Gal-GlcNAc-Fuc(SO3)-GalNAc-Fuc structure 23
Gal-GalNAc-Ara(SO3)-GlcNAc-Fuc structure 24
Gal-GalNAc-Ara(SO3)-GalNAc-Fuc structure 25
Gal-GlcNAc-Ara(SO3)-GalNAc-Fuc structure 26
GlcNAc-Fuc(SO3)-GlcNAc-Fuc-Fuc structure 27
GlcNAc-Ara(SO3)-GlcNAc-Fuc-Fuc structure 28
GalNAc-Fuc(SO3)-GlcNAc-Fuc-Fuc structure 29
GalNAc-Fuc(SO3)-GalNAc-Fuc-Fuc structure 30
GlcNAc-Fuc(SO3)-GalNAc-Fuc-Fuc structure 31
GalNAc-Ara(SO3)-GlcNAc-Fuc-Fuc structure 32
GalNAc-Ara(SO3)-GalNAc-Fuc-Fuc structure 33
GlcNAc-Ara(SO3)-GalNAc-Fuc-Fuc.
```

2. A polysaccharide having a structure selected from the group consisting of the following structures:

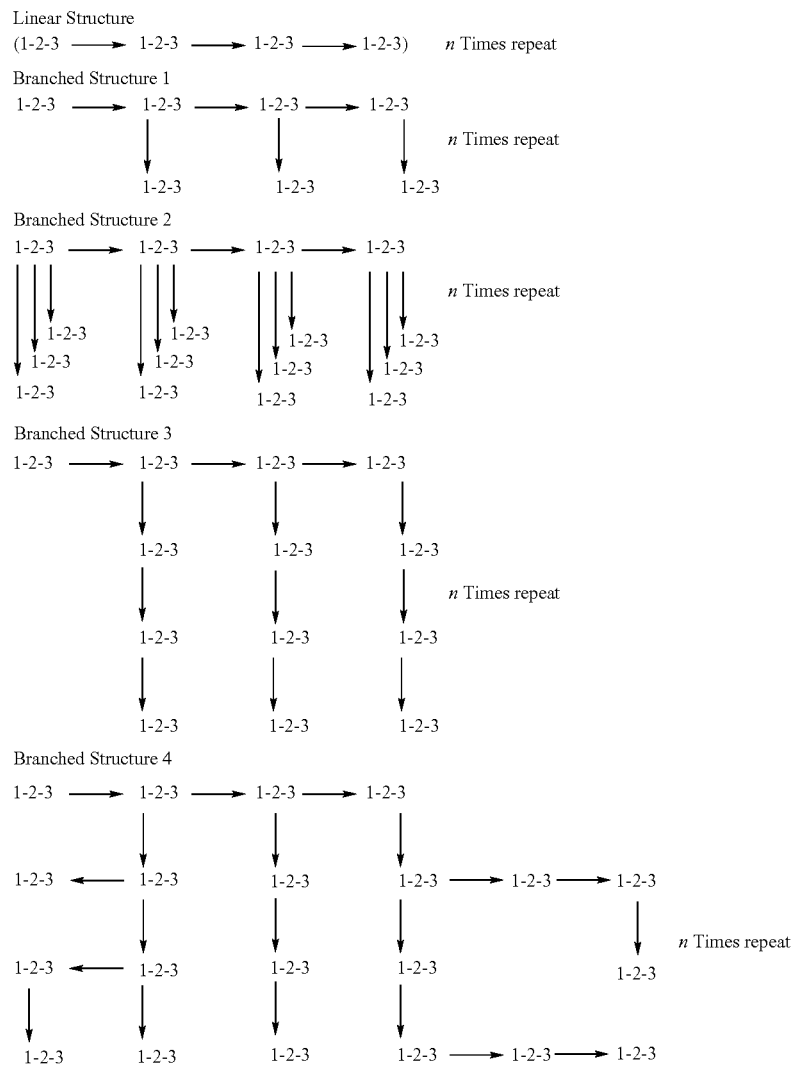

Wherein the number 1 represents GlcNAc monosaccharide, the number 2 represents fucose monosaccharide, and the number 3 represents (SO$_3$)Gal monosaccharide, and wherein the molecular weight is less than 1000 kD.

3. A method of stimulating proliferation of any mammalian NK cells and/or .gamma..delta.T cells of mammal, comprising contacting said cells with a at least one compound selected from the compounds of claim 2.

4. A method for treating an animal afflicted with a disease selected from the group consisting of melanoma, lymphoma, breast ductal carcinoma, colon carcinoma and herpes virus infection, comprising the steps of administering an active ingredient which is a at least one structure selected from the group consisting of the compounds of claim 2, to living NK or .gamma..delta.T cells to proliferate the growth of said cells and then administering said proliferated cells to said animal.

5. An oligosaccharide of structure 2,
Structure 2
GlcNAcβ1-3Fuc
3SO$_3$.

6. A pharmaceutical composition comprising at least of one compound of claim 1, 2, or 5.

7. A pharmaceutical composition according to claim 6, with an inactive, pharmaceutically acceptable carrier, diluent or excipient.

8. A pharmaceutical composition according to claim 6 for stimulating selectively the proliferation of mammalian NK cells or .gamma..delta.T cells.

9. A method of stimulating proliferation of any mammalian NK cells and/or .gamma..delta.T cells of mammal, comprising contacting said cells with a at least one compound selected from the compounds of claim 1 or 5.

10. A method for treating an animal afflicted with a disease selected from the group consisting of melanoma, lymphoma, breast ductal carcinoma, colon carcinoma and herpes virus infection, comprising the steps of administering an active ingredient which is a at least one structure selected from the group consisting of the compounds of claim 1 or 5 to living NK or .gamma..delta.T cells to proliferate the growth of said cells and then administering said proliferated cells to said animal.

* * * * *

SEQUENCE LISTING

<160> NUMBER OF SEQ ID NOS: 8

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Leu Phe Thr Val Pro Ile Tyr Val Pro Glu Asp Gln Leu
 1               5                  10

<210> SEQ ID NO 2
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Pro Glu Val Gly Val Pro Ile Tyr Val Pro Glu Asp Gln Leu
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Pro Val Val Gly Val Pro Ile Tyr Val Pro Glu Asp Gln Leu
 1               5                  10

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Phe Val Val Met Arg
 1               5

<210> SEQ ID NO 5
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Pro Gln Asp Pro Phe
 1               5

<210> SEQ ID NO 6
<211> LENGTH: 6
<212> TYPE: PRT
<213> ORGANISM: Artificial Sequence -continued

```
<220> FEATURE:
<223> OTHER INFORMATION: Description of Artificial Sequence: Synthetic
      peptide

<400> SEQUENCE: 6

Leu Ala Gly Val Val Ile
  1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Pro Gln Ala Ser Ser Gly
  1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ala Ala Gln Trp Ile Gly Gln Lys
  1               5
```